United States Patent
Choi

(10) Patent No.: US 10,444,177 B2
(45) Date of Patent: Oct. 15, 2019

(54) NO CODING TYPE BIOSENSOR AND METHOD FOR MANUFACTURING THE SAME

(71) Applicant: BBB Inc., Seongnam-si, Gyeonggi-do (KR)

(72) Inventor: Jaekyu Choi, Seongnam-si (KR)

(73) Assignee: BBB INC., Seongnam-si, Gyeonggi-do (KR)

(*) Notice: Subject to any disclaimer, the term of this patent is extended or adjusted under 35 U.S.C. 154(b) by 543 days.

(21) Appl. No.: 15/164,869

(22) Filed: May 26, 2016

(65) Prior Publication Data

US 2016/0349203 A1    Dec. 1, 2016

(30) Foreign Application Priority Data

May 26, 2015 (KR) .......................... 10-2015-0073230
May 23, 2016 (KR) .......................... 10-2016-0062944

(51) Int. Cl.
*G01N 27/327* (2006.01)

(52) U.S. Cl.
CPC .............................. *G01N 27/3272* (2013.01)

(58) Field of Classification Search
CPC ........................................ G01N 27/327–3274
See application file for complete search history.

(56) References Cited

U.S. PATENT DOCUMENTS

| | | | |
|---|---|---|---|
| 2013/0027064 A1* | 1/2013 | Austera | G01N 27/3272 324/692 |
| 2013/0122532 A1 | 5/2013 | Hsiao et al. | |
| 2015/0047977 A1 | 2/2015 | Liu et al. | |
| 2015/0068893 A1* | 3/2015 | Lee | G01N 27/3272 204/403.04 |

FOREIGN PATENT DOCUMENTS

| | | |
|---|---|---|
| KR | 10-2012-0133029 A | 12/2012 |
| KR | 10-2013-0030867 A | 3/2013 |

OTHER PUBLICATIONS

Korean Office Action for corresponding Korean Patent Application No. 10-2015-0073230 dated Jul. 27, 2015.

\* cited by examiner

*Primary Examiner* — J. Christopher Ball
(74) *Attorney, Agent, or Firm* — Hauptman Ham, LLP

(57) ABSTRACT

Provided is a non-coding type biosensor. The non-coding type biosensor includes a first electrode including a first sub-electrode and a plurality of second sub-electrodes that are spaced apart from the first sub-electrode, ends of at least some of the plurality of second sub-electrodes being connected to the first sub-electrode, a reaction chamber in which a target material and a mixture solution react with each other, the reaction chamber contacting opposite ends of the plurality of second sub-electrodes, and a second electrode of which one end contacts the reaction chamber.

11 Claims, 13 Drawing Sheets

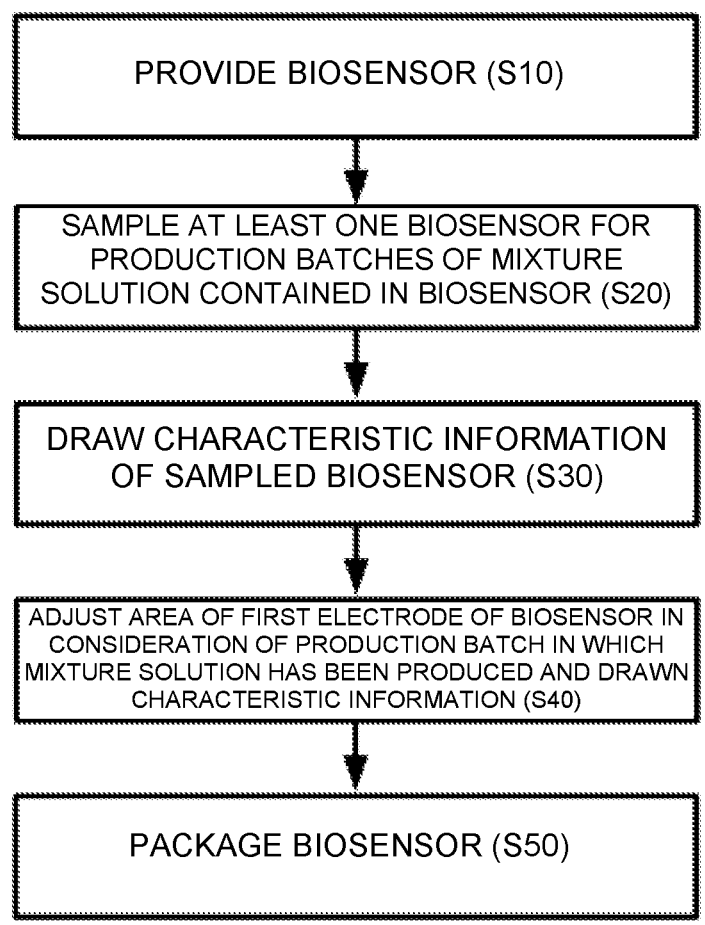

NO CODING TYPE BIOSENSOR AND METHOD FOR MANUFACTURING THE SAME

CROSS-REFERENCE TO RELATED APPLICATIONS

A claim for priority under 35 U.S.C. § 119 is made to Korean Patent Applications No. 10-2015-0073230 filed May 26, 2015 and Korean Patent Applications No. 10-2016-0062944 filed May 23, 2016, in the Korean Intellectual Property Office, the entire contents of which are hereby incorporated by reference.

BACKGROUND

The inventive concept relates to a non-coding type biosensor and a method for manufacturing the same, and more particularly to a non-coding type biosensor that may adjust an area of a working electrode of the biosensor according to characteristics of a mixture solution contained in the biosensor in a process of manufacturing the biosensor in order to omit a process of reading a code related to the biosensor when the manufactured biosensor is used, and a method for manufacturing the same.

An electrochemical biosensor may detect an electrochemical signal (for example, an intensity of a current) through an electrode when a target material (for example, blood) and a mixture solution (for example, a mixture solution of an enzyme and a polymer) react with each other in the electrochemical biosensor. Accordingly, the electrochemical biosensor may monitor an index for a target material, and when the target material is a biological liquid including blood, an index related to the health of a person, from which blood is collected, may be monitored through the electrochemical biosensor.

Meanwhile, in the electrochemical biosensor, an enzyme mixture of an enzyme and a polymer may be used as a mixture solution, and the characteristics of the enzyme mixture may vary according to a manufacturing environment such as temperature or humidity. Accordingly, when the electrochemical biosensor is manufactured by using the mixture solutions produced in different production batches, the magnitude of a current obtained as a result of a reaction may vary for the same target material.

For this reason, the reaction result should be calibrated so that a correct result may be obtained by correcting errors due to the characteristics of the mixture solution, and a process of providing calibration information to a reader such that the reader that reads information of the biosensor performs a calibration is generally called coding.

SUMMARY

Coding is a process that is necessary to obtain a correct result, but a code chip containing calibration information should be prepared for coding or a troublesome step, for example, of inputting specific information to a reader by the user may be necessary. In addition, although coding may be performed by giving a color chip, a resistance, or a unique pattern to a biosensor in advance, the user may feel unsatisfied in the coding process because calibration information corresponding to the color, the resistance, or the unique pattern is stored in the reader in advance, the user may feel uncomfortable in the coding process. Accordingly, development of a coding method that avoids causing inconvenience to the user is urgent.

The inventive concept has been made in an effort to solve the above-mentioned problems, and provides a non-coding type biosensor that allows coding without requesting an additional step from the user, and a method for manufacturing the same.

The inventive concept also provides an automatically coded electrochemical biosensor that allows coding by adjusting an area of a working electrode, and a method for manufacturing the same. The inventive concept also provides a non-coding type biosensor that calibrates the biosensor in a hardware manner by reflecting characteristics of a mixture solution in a process of manufacturing the biosensor, and a method for manufacturing the same.

The inventive concept also provides a non-coding biosensor that omits a coding step in a process of using the biosensor by adjusting an area of a working electrode in a process of manufacturing the biosensor, and a method for manufacturing the same.

The inventive concept also provides a non-coding biosensor that efficiently realizes a desired resolution in a process of adjusting an area of a working electrode of the biosensor, and a method for manufacturing the same.

The technical objects of the inventive concept are not limited to the above-mentioned one, and the other unmentioned technical objects will become apparent to those skilled in the art from the following description.

In accordance with an aspect of the inventive concept, there is provided a non-coding type biosensor including a first electrode including a first sub-electrode and a plurality of second sub-electrodes that are spaced apart from the first sub-electrode, ends of at least some of the plurality of second sub-electrodes being connected to the first sub-electrode, a reaction chamber in which a target material and a mixture solution react with each other, the reaction chamber contacting opposite ends of the plurality of second sub-electrodes, and a second electrode of which one end contacts the reaction chamber.

In accordance with another aspect of the inventive concept, there is provided a non-coding type biosensor including a first electrode including a first sub-electrode and a plurality of second sub-electrodes, the first sub-electrode including a body part and a working part, and a reaction chamber in which a mixture solution that reacts with a target material is located, the reaction chamber contacting the working part and the plurality of second sub-electrodes.

In accordance with another aspect of the inventive concept, there is provided a method for manufacturing a non-coding type biosensor including providing a biosensor including first and second electrodes, and a reaction chamber that contacts the first and second electrodes and in which a target material and a mixture solution react with each other, and adjusting an area of the first electrode according to the mixture solution.

In accordance with another aspect of the inventive concept, there is provided a method for manufacturing a non-coding type biosensor including providing a biosensor including first and second electrodes, and a reaction chamber that contacts the first and second electrodes, wherein a mixture solution that reacts with a target material is located in the reaction chamber, the first electrode is a working electrode, and the second electrode is a reference electrode, sampling at least one biosensor for production batches of the mixture solution contained in the biosensor, drawing characteristic information of the sampled biosensor, and adjusting an area of the first electrode of the biosensor in consideration of the production batch in which the mixture solution contained in the biosensor has been produced and the drawn characteristic information.

According to the inventive concept, the following effects may be obtained but the effects of the inventive concept are not limited thereto.

First, because coding is automatically performed by using an existing working electrode instead of adding a separate electrode for automatic coding, costs and time for manufacturing an electrochemical biosensor can be reduced.

Second, because an area of a working electrode may be adjusted according to characteristics of a mixture solution contained in a biosensor in a manufacturing process, a calibrated reaction result can be obtained without any separate coding process in a process of using a biosensor and thus the user can be provided with convenience.

Third, because an area of a working electrode may be controlled by controlling a connection relationship of a deposited working electrode instead of additionally providing a color chip, a resistance, or a unique pattern to a biosensor, costs and time for manufacturing the biosensor can be reduced.

Fourth, because areas of a plurality of second sub-electrodes have a certain relationship, a desired resolution can be efficiently realized in a process of adjusting an area of a working electrode of a biosensor.

The effects of the inventive concept can be achieved by the configurations of the inventive concept irrespective of whether or not they are recognized by the inventor(s). Therefore, the aforementioned effects are merely examples and should not be construed that the inventor(s) describes all effect recognized by the inventor(s) or actually present. The effects of the inventive concept should be additionally recognized by the overall description of the specification, and the effects that are admitted by those skilled in the art throughout the specification also within the range of the effects of the inventive concept.

BRIEF DESCRIPTION OF THE FIGURES

The above and other objects and features will become apparent from the following description with reference to the following figures, wherein like reference numerals refer to like parts throughout the various figures unless otherwise specified, and wherein

FIG. 13 is a flowchart of a method for manufacturing the non-coding type biosensors according to the second to fourth embodiments of the inventive concept.

DETAILED DESCRIPTION

Figure 1:
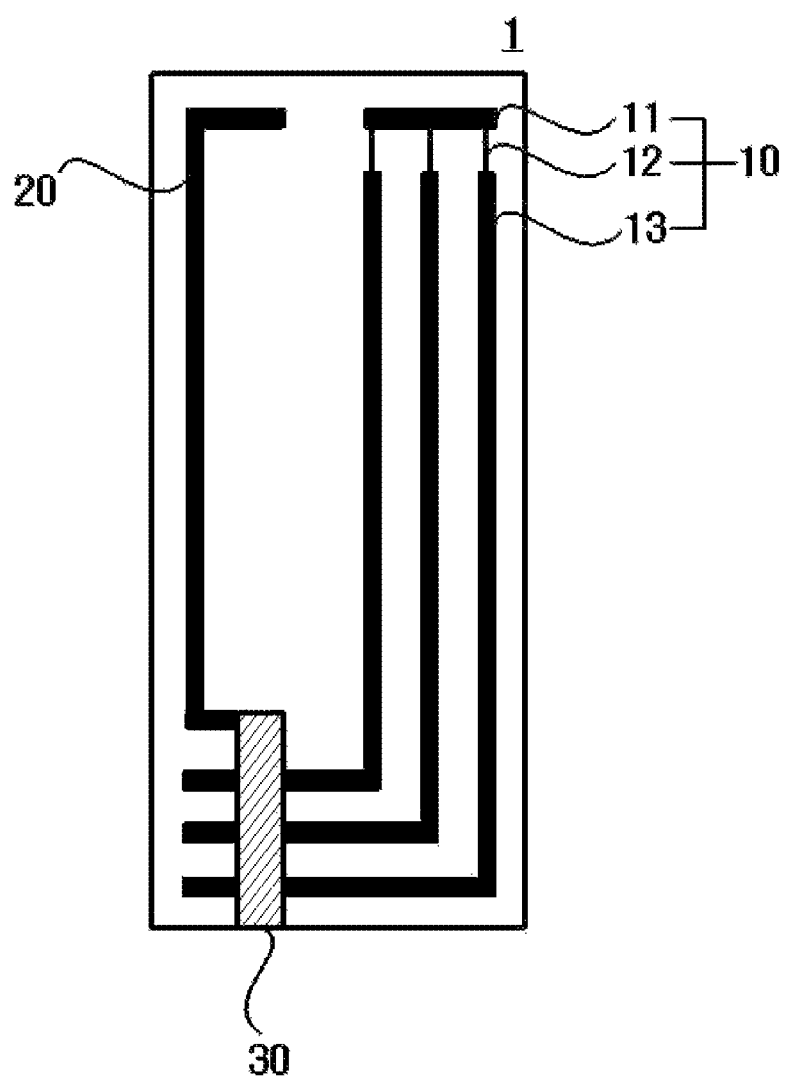
FIGS. 1 and 2 are views illustrating a schematic configuration of a non-coding type biosensor according to a first embodiment of the inventive concept.

Prior to the description of the inventive concept, it will be noted that the terms and wordings used in the specification and the claims should not be construed as general and lexical meanings, but should be construed as the meanings and concepts that agree with the technical spirits of the inventive concept, based on the principle stating that the concepts of the terms may be properly defined by the inventor(s) to describe the invention in the best manner.

Therefore, because the examples described in the specification and the configurations illustrated in the drawings are merely for the preferred embodiments of the inventive concept but cannot represent all the technical spirits of the inventive concept, it should be understood that various equivalents and modifications that may replace them can be present.

Hereinafter, the inventive concept will be described in more detail with reference to the drawings. The terms "sensor", "module" and "unit" for the elements are given or used in combination to easily write the specification, and do not have distinguished meanings or functions.

Figure 2:
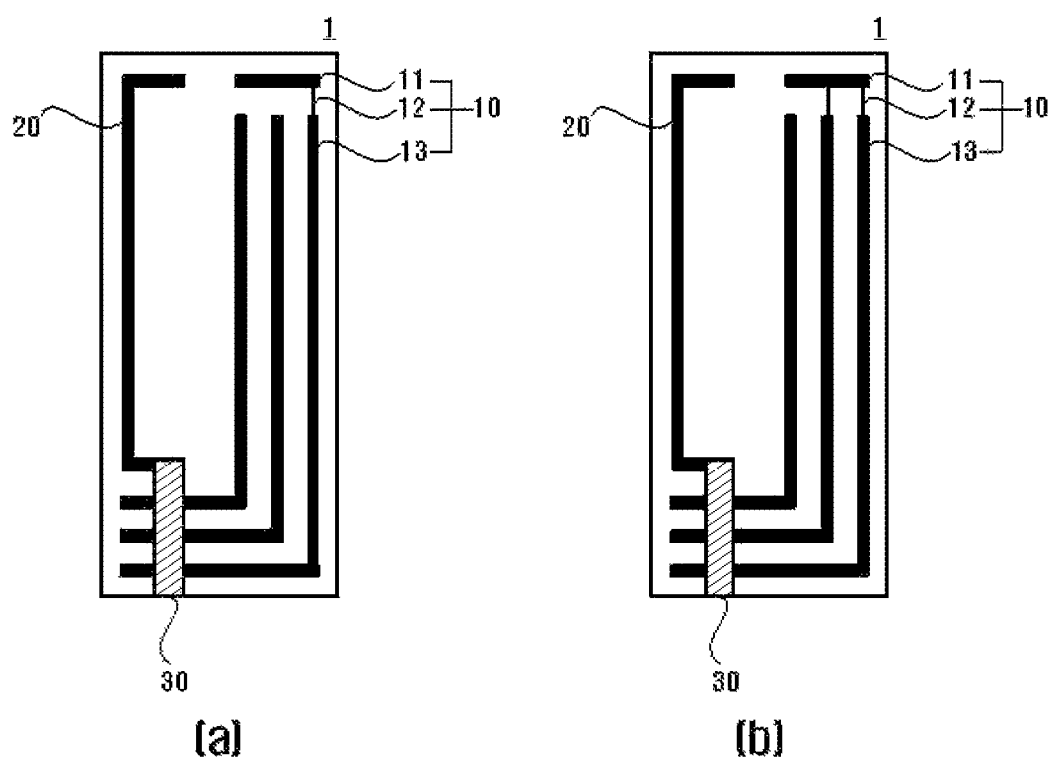

Hereinafter, a non-coding type biosensor 1 according to a first embodiment of the inventive concept will be described with reference to FIGS. 1 to 3. Referring to FIGS. 1 and 2, the drawings illustrating a schematic configuration of the non-coding type biosensor 1 according to the first embodiment of the inventive concept are disclosed, and referring to FIG. 3, a schematic configuration of a medical device 100 that may use the biosensor 1 of FIG. 1 is disclosed.

The biosensor 1 according to the first embodiment of the inventive concept is a biosensor for electrochemical analysis, and may be used to measure and monitor biometric information of the user. The biosensor 1 may be implemented as a module, for example, with a strip form, but the inventive concept is not limited thereto.

Figure 3:
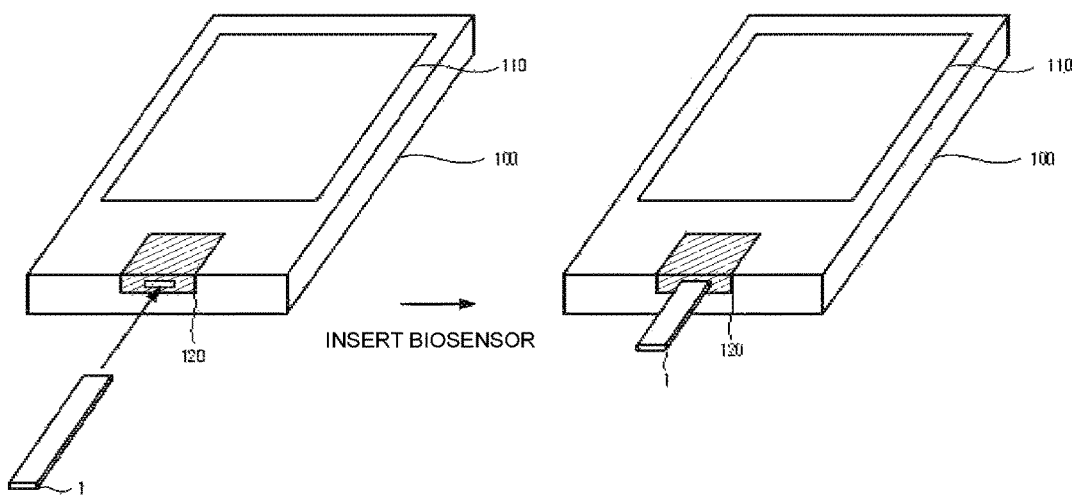
FIG. 3 is a view illustrating a schematic configuration of a medical device that may use the biosensor of FIG. 1.

In detail, referring to FIGS. 1 to 3, the biosensor 1 may include a first electrode 10, a second electrode 20, and a reaction chamber 30. However, in some embodiments, a biosensor 1 including a larger number of elements than that of the elements of FIG. 1 may be implemented, or may a biosensor 1 including a smaller number of elements than that of the elements of FIG. 1 may be implemented.

The first electrode 10, for example, may be a working electrode, but the inventive concept is not limited thereto. The first electrode 10 may include a first sub-electrode 11 and a plurality of second sub-electrodes 13 that are spaced apart from the first sub-electrode 11, and ends of at least some of the plurality of second sub-electrodes 13 may be connected to the first sub-electrode 11.

For example, referring to FIG. 1, ends of all of the plurality of second sub-electrodes 13 may be electrically connected to the first sub-electrode but the inventive concept is not limited thereto, and referring to FIGS. 2A and 2B, only ends of some of the plurality of second sub-electrodes 13 may be electrically connected to the first sub-electrode 11 and for example, at least some of the plurality of second sub-electrodes 13 may not be electrically connected to the first sub-electrode 11.

Here, it may be determined according to a mixture solution in a reaction chamber 30, which will be described below, whether ends of some of the plurality of second sub-electrodes 13 are electrically connected to the first sub-electrode 11. That is, the number of the second sub-electrodes 13, which are not electrically connected to the first sub-electrode 11, of the plurality of second sub-electrodes 13 may vary according to the mixture solution in the reaction chamber 30. In detail, the number of the second sub-electrodes 13, of which ends are connected to the first sub-electrode 11, of the plurality of second sub-electrodes 13 may be determined according to in which batch the mixture solution in the reaction chamber 30 is produced. The biosensor 1 uses an enzyme mixture as the mixture solution (for example, a reagent), and because the magnitude of a current that is output as a reaction resultant for a target material (or a biological sample) of the same concentration may vary according to a production batch in the case of an enzyme mixture, it is necessary to perform different calibrations for different production batches of the enzyme mixture.

The biosensor 1 according to the first embodiment of the inventive concept uses the fact that a surface area of an electrode is proportional to the intensity of an output current. That is, a surface area of an electrode that may act as the first electrode 10 may be determined according to the number of the second sub-electrodes 13, of which ends are electrically connected to the first sub-electrode 11, of the plurality of second sub-electrodes 13, and accordingly, the intensity of an output current may be adjusted.

For example, because a surface area of the first electrode 10 may be enlarged when ends of a larger number of second sub-electrodes 13 are electrically connected to the first sub-electrode 11, an intensity of an output current may become higher, whereas because a surface of the first electrode 10 may be narrowed when ends of a smaller number of second sub-electrodes 13 are electrically connected to the first sub-electrode 11, an intensity of an output current may become lower. Here, because a current does not flow through the second sub-electrodes 13, of which ends are not electrically connected to the first sub-electrode 11, of the plurality of second sub-electrodes 13, a surface area of the first electrode 10 is not influenced at all by the second sub-electrodes 13, of which ends are not electrically connected to the first sub-electrode 11.

Accordingly, in the biosensor 1 according to the present embodiment, the surface of the first electrode 10 may be adjusted by controlling electrical connection between the first sub-electrode 11 and the plurality of second sub-electrodes 13, and accordingly, coding may be made automatically. Accordingly, because it is not necessary for the user to perform a step of inputting a separate code in the biosensor 1 according to the present embodiment, a convenience of the user may be improved.

Meanwhile, in the first electrode 10, ends of at least some of the plurality of second sub-electrodes 13 may be connected to the first sub-electrode 11 through electrode fabricating areas 12.

Here, the electrode fabricating areas 12 may be configurations that are made to easily control electrical connections between the first sub-electrode 11 and the second sub-electrodes 13 in the biosensor 1. For example, the shapes of the electrode fabricating areas 12 may be different from the shapes of the plurality of second sub-electrodes 13, and for example, the widths of the electrode fabricating areas 12 may be smaller than the widths of the second sub-electrodes 13 but the inventive concept is not limited thereto. Accordingly, it is possible to easily remove the electrode fabricating areas 12 through a method such as radiation of a laser beam or punching.

Further, referring to FIGS. 1 and 2, the plurality of second sub-electrodes 13 may have the same area, but the inventive concept is not limited thereto.

Subsequently, the reaction chamber 30 may be a space in which a target material and a mixture solution that reacts with the target material may react with each other, and the reaction chamber 30 may contact opposite ends of the plurality of second sub-electrodes 13.

That is, because the plurality of second sub-electrodes 13 contact the reaction chamber 30, the reaction chamber 30 may form discontinuous contact points corresponding to the number of the second sub-electrodes 13 together with the first electrode 10. Accordingly, when the target material reacts with the mixture solution while passing through the reaction chamber 30, current peaks may be sequentially formed for the respective contact points. Thus, because the first electrode 10 includes the plurality of second sub-electrodes 13 in the biosensor 1 according to the present embodiment, it may be identified whether the target material is introduced into the reaction chamber 30 sufficiently or at a suitable speed.

Here, the target material may be a biological liquid such as blood, limp liquid, or tissue liquid but the inventive concept is not limited thereto, and the mixture solution may be an enzyme mixture but the inventive concept is not limited thereto.

In addition, one end of the second electrode 20 may contact the reaction chamber 30.

Hereinafter, utilization of the biosensor 1 according to the present embodiment will be described with reference to FIG. 3.

That is, in the biosensor 1 according to the present embodiment, an area of the first electrode 10 may be adjusted by determining the number of the second sub-electrodes 13, which are not electrically connected to the first sub-electrode 11, of the plurality of second sub-electrodes 13 according to the mixture solution in the reaction chamber 30.

Accordingly, the user may obtain an accurate result by directly inserting the biosensor 1 into the socket 120 of a medical device 100 including a display 110 without performing a separate step.

Because calibration is automatically performed according to the area of the first electrode 10, necessary monitoring data may be obtained by detecting a signal generated due to a reaction of the target material and the mixture solution.

Figure 4:
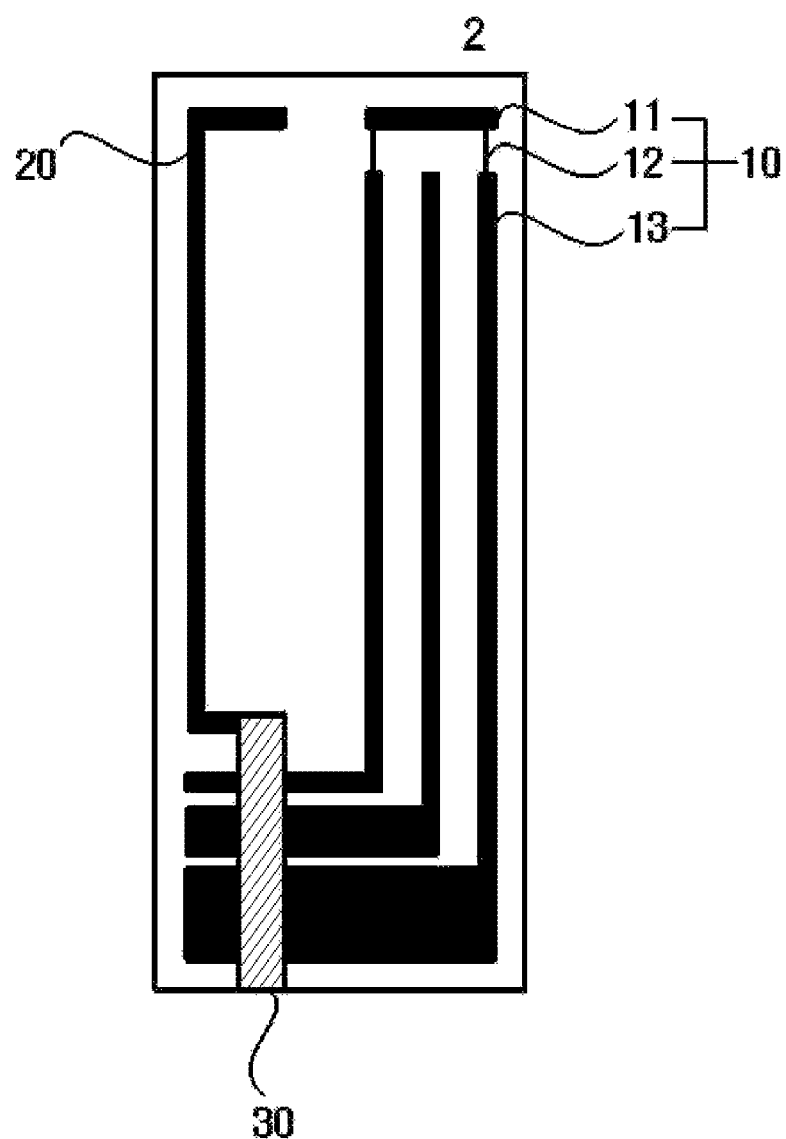
FIG. 4 is a view illustrating a schematic configuration of a non-coding type biosensor according to a second embodiment of the inventive concept.

Hereinafter, a non-coding type biosensor 2 according to a second embodiment of the inventive concept will be described with reference to FIG. 4. Meanwhile, a difference from the non-coding type biosensor 1 according to the first embodiment of the inventive concept will be mainly described. Referring to FIG. 4, a schematic configuration of the non-coding type biosensor 2 according to the second embodiment of the inventive concept is illustrated.

Referring to FIG. 4, at least some of the plurality of second sub-electrodes 13 may have different areas. For example, all of the plurality of second sub-electrodes 13 may have different areas, but the inventive concept is not limited thereto.

According to the biosensor 2 of the present embodiment, a resolution for adjusting a current for calibration may be determined by making the areas of the plurality of second sub-electrodes 13 different.

Figure 5:
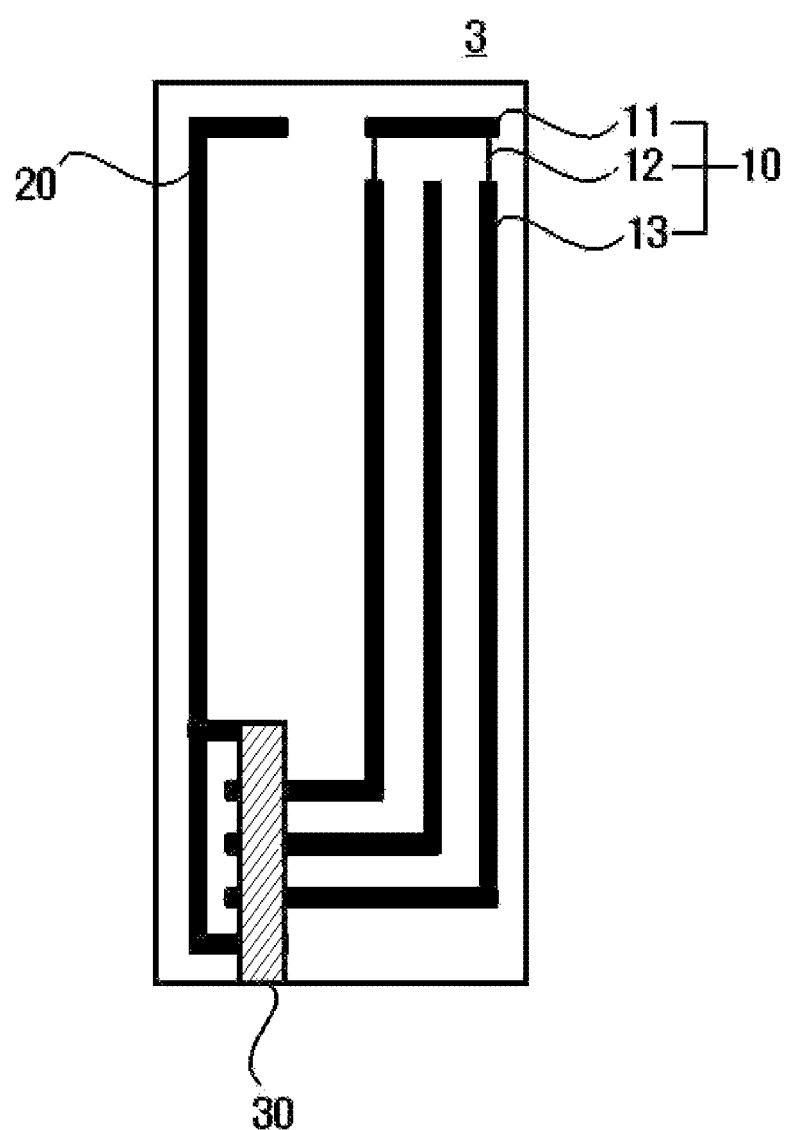
FIG. 5 is a view illustrating a schematic configuration of a non-coding type biosensor according to a third embodiment of the inventive concept.

Hereinafter, a non-coding type biosensor 3 according to a third embodiment of the inventive concept will be described with reference to FIG. 5. Meanwhile, a difference from the non-coding type biosensor 1 according to the first embodiment of the inventive concept will be mainly described. Referring to FIG. 5, a schematic configuration of the non-coding type biosensor 3 according to the third embodiment of the inventive concept is illustrated.

Referring to FIG. 5, the form of the second electrode 20 may be different from that of the second electrode 20 of FIG. 1, but the form of the second electrode 20 is not limited thereto.

Figure 6:
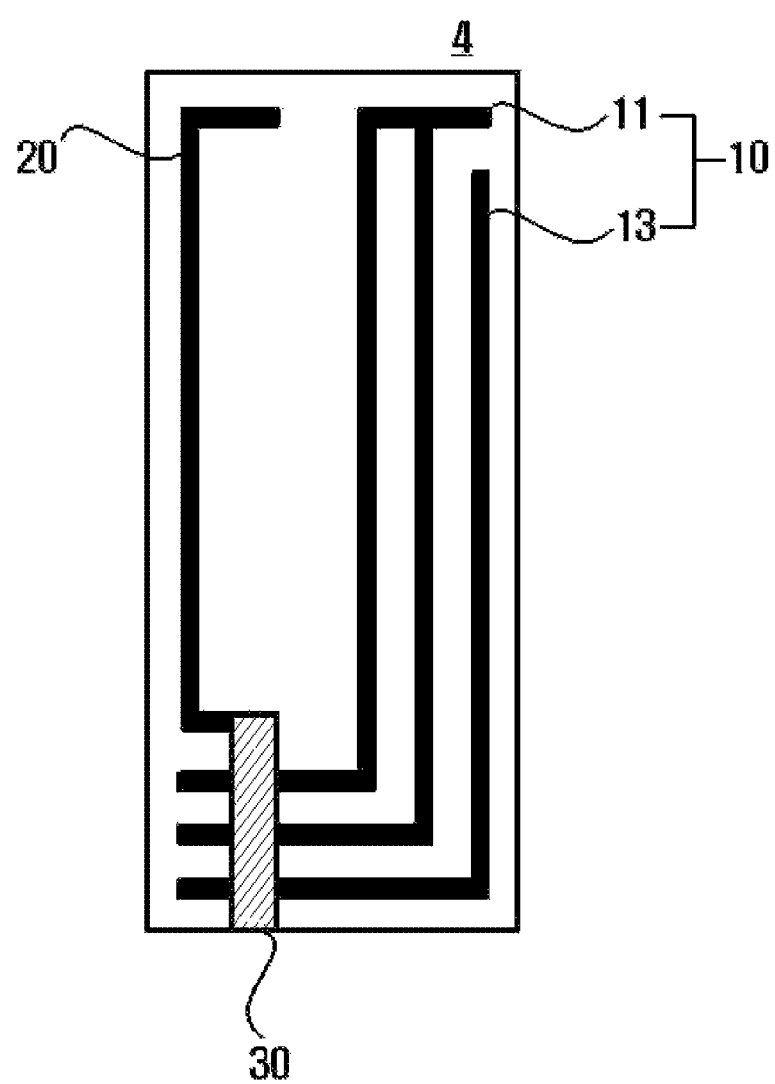
FIG. 6 is a view illustrating a schematic configuration of a non-coding type biosensor according to a fourth embodiment of the inventive concept.

Hereinafter, a non-coding type biosensor 4 according to a fourth embodiment of the inventive concept will be described with reference to FIG. 6. Meanwhile, a difference from the non-coding type biosensor 1 according to the first embodiment of the inventive concept will be mainly described. Referring to FIG. 6, a schematic configuration of the non-coding type biosensor 4 according to the fourth embodiment of the inventive concept is illustrated.

Referring to FIG. 6, in the first electrode 10, ends of at least some of the plurality of second sub-electrodes 13 may be directly connected to the first sub-electrode 11. That is, the non-coding type biosensor 4 according to the inventive concept may not include an electrode fabricating area 12.

Accordingly, when at least some of the plurality of second sub-electrodes 13 are neither electrically nor directly connected to the first sub-electrode 11 in the first electrode 10, the first electrode 10 may be one in which some of the second electrodes 13 are moved through a method such as radiation of a laser beam or punching.

Hereinafter, a non-coding type biosensor according to the fifth embodiment of the inventive concept will be described. Meanwhile, a difference from the non-coding type biosensor 1 according to the first embodiment of the inventive concept will be mainly described.

In the first electrode 10 of the non-coding type biosensor according to the present embodiment, the number of the second sub-electrodes 13, of which ends are electrically connected to the first sub-electrode 11, of the plurality of second sub-electrodes 13 may be determined not according to the mixture solution (for example, a sample or a reagent) in the reaction chamber 30 but according to which kind of biomarker is measured by the biosensor.

Accordingly, the shape of the first electrode 10 may function as an identifier that provides information by which the medical device 100 identifies a biomarker that is a measurement target.

Figure 7:
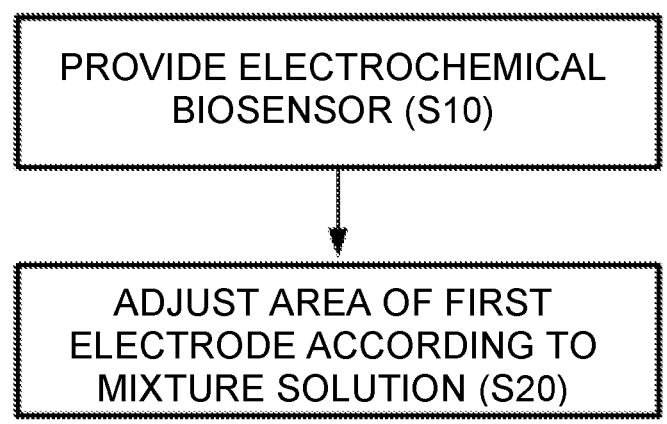
FIG. 7 is a flowchart of a method for manufacturing the non-coding type biosensor according to the first embodiment of the inventive concept.

Hereinafter, a method for manufacturing the non-coding type biosensor 1 according to the first embodiment of the inventive concept will be described with reference to FIG. 7. Referring to FIG. 7, a flowchart of the method for manufacturing the non-coding type biosensor 1 according to the first embodiment of the inventive concept is disclosed.

Referring to FIG. 7, the method for manufacturing the non-coding type biosensor 1 according to the present embodiment may, first, provide a biosensor 1 including first and second electrodes 10 and 20 and a reaction chamber 30 which contacts the first and second electrodes 10 and 20 and in which a target material and a mixture solution may react with each other (S10).

Here, the biosensor may be the biosensors described through the first to fifth embodiments but the inventive concept is not limited thereto, and the biosensor may be a biosensor 1 of the following embodiment.

For example, the step of providing the biosensor 1 may be a step of providing a biosensor 1 including a first electrode 10 that includes a first sub-electrode 11 and a plurality of second sub-electrodes 13 that are spaced apart from the first sub-electrode 11, a reaction chamber 30 in which a target material and a mixture solution react with each other, the reaction chamber 30 contacting opposite ends of the plurality of second sub-electrodes 13, and a second electrode 20 of which one end contacts the reaction chamber 30, but the inventive concept is not limited thereto.

Next, referring to FIG. 7, an area of the first electrode 10 may be adjusted according to a mixture solution (for example, a reagent) (S20).

Here, the step of adjusting the area of the first electrode 10 according to the mixture solution may be a step of removing at least a portion of the first electrode 10, and for example, a laser beam radiating method or a punching method may be used but the inventive concept is not limited thereto.

In some embodiments, the step of adjusting the area of the first electrode 10 according to the mixture solution may be a step of interrupting electrical connections of the first sub-electrode 11 and the plurality of second sub-electrodes 13, but the inventive concept is not limited thereto.

Hereinafter, a non-coding type biosensor and a method for manufacturing the same according to another embodiment of the inventive concept will be described.

Figure 8:
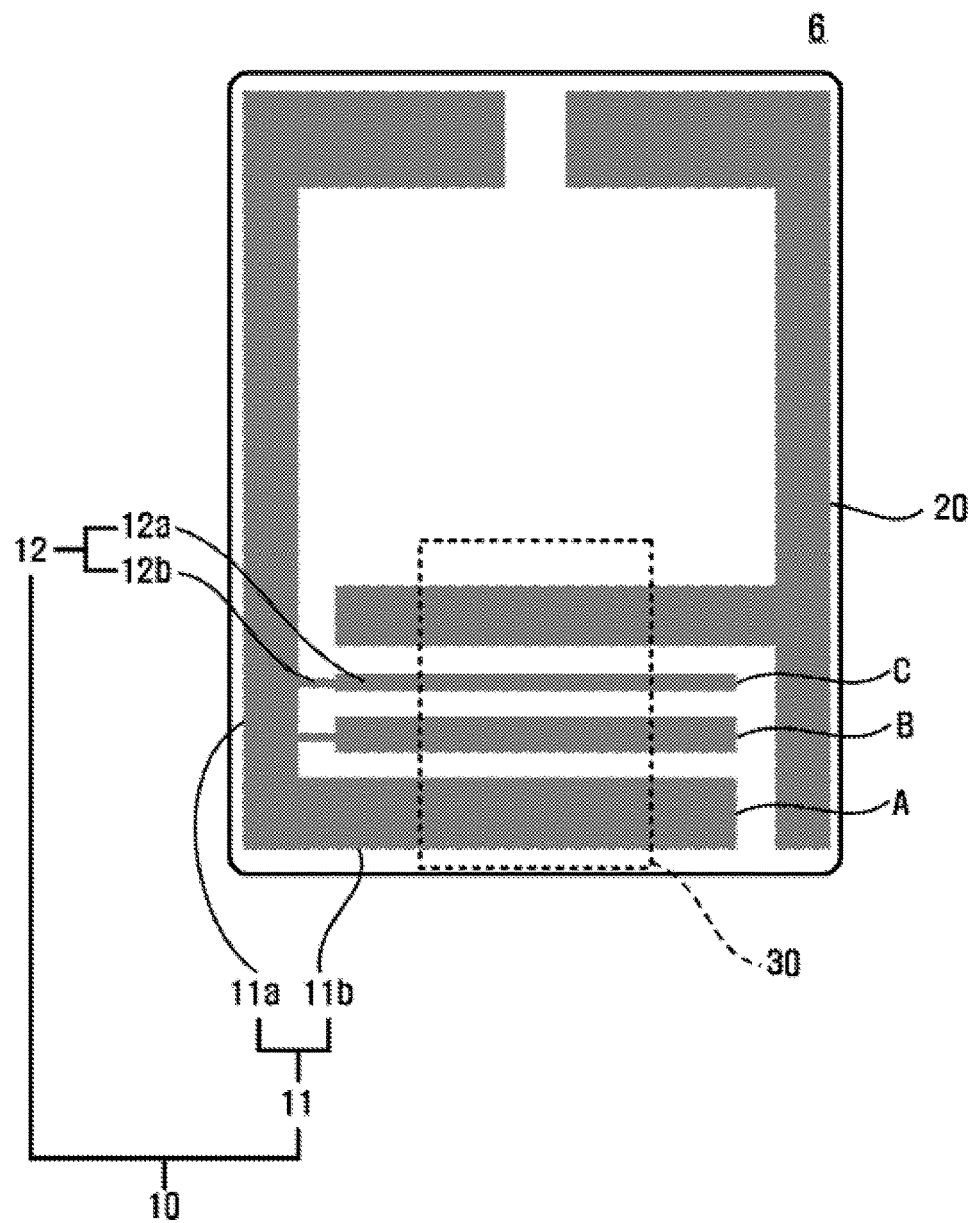
FIGS. 8 and 9 are views illustrating a schematic configuration of a non-coding type biosensor according to a sixth embodiment of the inventive concept.
Figure 9:
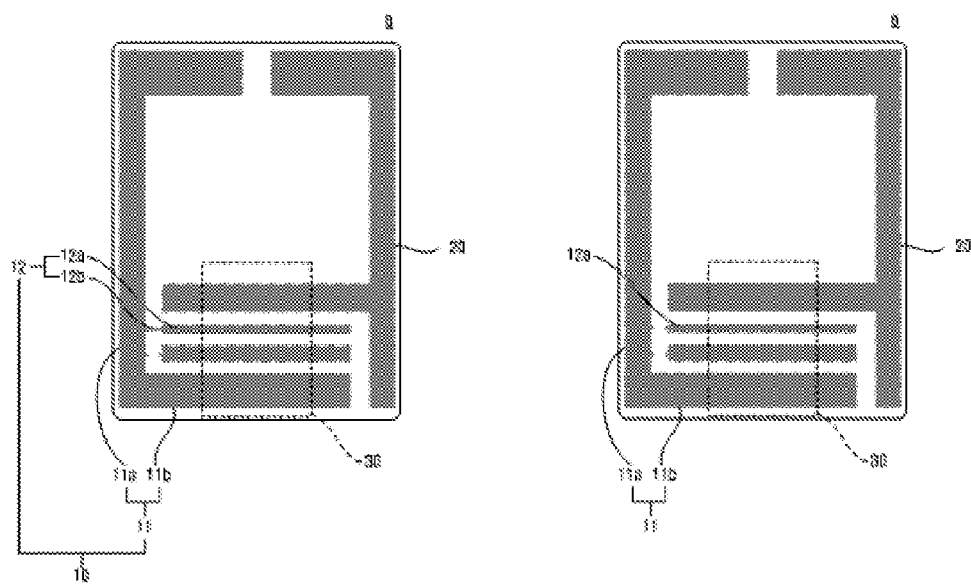
Figure 10:
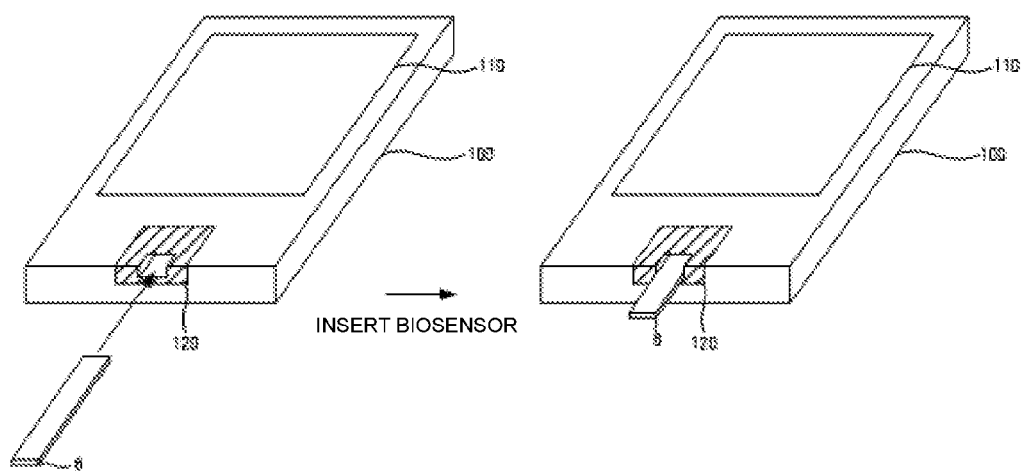
FIG. 10 is a view illustrating a schematic configuration of a medical device that may use the biosensor of FIG. 8.

Hereinafter, a non-coding type biosensor 6 according to a sixth embodiment of the inventive concept will be described with reference to FIGS. 8 to 10. Referring to FIGS. 8 and 9, the drawings illustrating a schematic configuration of the non-coding type biosensor 6 according to the sixth embodiment of the inventive concept are disclosed, and referring to FIG. 10, a schematic configuration of a medical device that may use the biosensor 6 of FIG. 8 is disclosed.

The biosensor 6 according to the sixth embodiment of the inventive concept may be a biosensor 6 for electrochemical analysis, but the inventive concept is not limited thereto. Further, the biosensor 6 according to the present embodiment may be used to measure and monitor biometric information of the user and for example, may has a strip form, but the inventive concept is not limited thereto.

In detail, referring to FIG. 8, the biosensor 6 may include a first electrode 10, a second electrode 20, and a reaction chamber 30, wherein the first electrode 10 may be a working electrode and a second electrode 20 may be a reference electrode, but the inventive concept is not limited thereto. In some embodiments, a biosensor 6 including a larger number of elements than that of the elements of FIG. 8 may be implemented, or may a biosensor 6 including a smaller number of elements than that of the elements of FIG. 8 may be implemented.

The first electrode 10 may include a first sub-electrode 11 and a plurality of second sub-electrodes 12. Here, the area of the first electrode 10 acting as a working electrode may vary according to a connection relationship between the first electrode 10 and the plurality of second sub-electrodes 12.

Referring to FIG. 8, ends of all of the plurality of second sub-electrodes 12 may be connected to the first sub-electrode 11, and because all of the first sub-electrode 11 and the plurality of second sub-electrodes 12 may function as working electrodes in this case, the area of the first electrode 10 functioning as a working electrode may be largest.

Referring to FIG. 9A, only ends of some of the plurality of second sub-electrodes 12 may be connected to the first sub-electrode 11, and in this case, the first sub-electrode 11 and the some second sub-electrodes 12 may function as working electrodes.

Referring to FIG. 9B, none of the plurality of second sub-electrodes 12 is not connected to the first sub-electrode 11, and because only the first sub-electrode 11 may function as a working electrode in this case, the area of the first electrode 10 functioning as a working electrode may be smallest.

It may be determined according to the characteristic of the mixture solution in a reaction chamber 30, which will be described below, whether ends of some of the plurality of second sub-electrodes 12 are electrically connected to the first sub-electrode 11. Further, the characteristics of the mixture solution may vary according to the environment of a production batch by which the mixture solution has been produced, and as a result, the number of ends of the second sub-electrodes, which is to be electrically connected to the first sub-electrode 11, of the plurality of second sub-electrodes 12 may be determined according to by which batch the mixture solution in the reaction chamber 30 has been produced.

In detail, an enzyme mixture of an enzyme and a polymer may be used as the mixture solution applied to the biosensor 6, and the characteristics of the enzyme mixture may vary according to a manufacturing environment such as temperature or humidity. Accordingly, the magnitude of a current that is output as a result of a reaction of a mixture solution and a target material according to by which product batch the corresponding solution has been produced. Accordingly, it is necessary to perform a calibration to remove an error generated according to the characteristics of the mixture solution, and it is necessary to perform different calibrations for different production batches of the mixture solution.

The biosensor 6 according to the sixth embodiment of the inventive concept may be calibrated in a hardware manner by using the fact that the surface area (or area) of a working electrode is proportional to the intensity of an output current. That is, a surface area of the first electrode 10 that may act as a working electrode may be determined according to the number of the second sub-electrodes 12, of which ends are electrically connected to the first sub-electrode 11, of the plurality of second sub-electrodes 12, and accordingly, the intensity of an output current may be adjusted.

For example, because a surface area of the first electrode 10 functioning as a working electrode may be enlarged when ends of a larger number of second sub-electrodes 12 are electrically connected to the first sub-electrode 11, an intensity of an output current may become higher, whereas because a surface of the first electrode 10 functioning as a working electrode may be narrowed when ends of a smaller number of second sub-electrodes 12 are electrically connected to the first sub-electrode 11, an intensity of an output current may become lower. Here, because a current does not flow through the second sub-electrodes 12, of which ends are not electrically connected to the first sub-electrode 11, of the plurality of second sub-electrodes 12, a surface area of the first electrode 10 functioning as a working electrode is not influenced at all by the second sub-electrodes 12, of which ends are not electrically connected to the first sub-electrode 11.

Accordingly, when it is determined whether a value of a current that is a reaction result is to be decreased or increased according to the characteristics of a mixture solution applied to the biosensor 6, a calibration may be performed in a manufacturing step by adjusting the number of the second sub-electrodes 12 connected to the first sub-electrode 11. That is, in the biosensor 6 according to the present embodiment, an area of the first electrode 10 functioning as a working electrode may be adjusted by controlling electrical connections of the first sub-electrode 11 and the plurality of second sub-electrodes 12, and because a hardware calibration is performed through this, a separate coding process is not necessary in the process of using the biosensor 6 later. Accordingly, because it is not necessary for the user to perform a step of inputting a separate code in the biosensor 6 according to the present embodiment, a convenience of the user may be improved.

Meanwhile, the first sub-electrode 11 may include a body part 11a and a working part 11b. The body part 11a may refer to an area of the first sub-electrode 11, which may be connected to the second sub-electrodes 12, and the working part 11b may refer to an area of the first sub-electrode 11, which contacts the reaction chamber 30. Referring to FIG. 8, the working part 11b may be arranged, for example, in parallel to the second sub-electrodes 12 to be spaced apart from the second sub-electrodes 12, but the inventive concept is not limited thereto.

In the present embodiment, because the working part 11b of the first sub-electrode 11 contacts the reaction chamber 30, an embodiment in which none of the plurality of sub-electrodes 12 is connected to the first sub-electrode 11 is also possible (see FIG. 9B). However, in an embodiment, the working part 11b of the first sub-electrode 11 is not electrically connected to the body part 11a, any one of the plurality of second sub-electrodes 12 should be connected to the body part 11a of the first sub-electrode 11.

Each of second sub-electrodes 12 may include an electrode adjusting part 12a and an electrode fabricating part 12b. The electrode adjusting part 12a may refer to an area of the second sub-electrodes 12, which contacts the reaction chamber 30, the electrode fabricating part 12b may refer to an area located between the electrode adjusting part 12a of the second sub-electrode 12 and the body part 11a of the first sub-electrode 11, and the configuration may be made to easily control an electrical connection of the first sub-electrode 11 and the second sub-electrode 12 in the biosensor 6.

For example, ends of at least some of the plurality of second sub-electrodes 12 may be connected to the body part 11a of the first sub-electrode 11 through the electrode fabricating parts 12b, respectively, and the shapes of the electrode fabricating parts 12b may be different from the shapes of the second sub-electrodes 12. In detail, the shapes of the electrode fabricating part 12b may be different from the shapes of the electrode adjusting parts 12a, and for example, the widths of the electrode fabricating parts 12b may be smaller than the widths of the electrode adjusting parts 12a to have a shape that may be easily removed, but the inventive concept is not limited thereto.

Accordingly, in the biosensor 6 according to the present embodiment, the electrode fabricating parts 12b may be easily removed in a method such as radiation of a laser beam or punching.

The second electrode 20 may be a reference electrode, and the second electrode 20 may contact the reaction chamber 30 while being spaced apart from the first electrode 10. However, a area of the second electrode 20 does not influence a magnitude of a current output as a result of the above-mentioned reaction.

The reaction chamber 30 may be a spacer, and a mixture solution that reacts with a target material may be located in the reaction chamber 30. Accordingly, the reaction chamber 30 may be a space in which the target material and the mixture solution may react with each other. The reaction chamber 30 may contact the body part 11a, the plurality of second sub-electrodes 12, and the second electrode 20.

Meanwhile, because the working part 11b of the first sub-electrode 11 and the plurality of second sub-electrodes 12 contact each other in the reaction chamber 30, the reaction chamber 30 may form discontinuous contact points corresponding to the number of the working parts 11b of the first sub-electrode 11 and the second sub-electrodes 12 together with the first electrode 10. Accordingly, when the target material reacts with the mixture solution while passing through the reaction chamber 30, current peaks may be sequentially formed for the respective contact points. Thus, because the first electrode 10 includes the plurality of second sub-electrodes 12 in the biosensor 6 according to the present embodiment, it may be identified whether the target material is introduced into the reaction chamber 30 sufficiently or at a suitable speed.

Here, the target material may be a biological liquid such as blood, limp liquid, or tissue liquid, but the inventive concept is not limited thereto. Meanwhile, referring to FIG. 8, in some embodiments, the area of the first sub-electrode 11 may be larger than the areas of the plurality of second sub-electrodes 12. In the present embodiment, because the first sub-electrode 11 always functions as a working electrode and a hardware calibration is performed by determining whether the second sub-electrodes 12 is to function as working electrodes, the areas of the second sub-electrodes 12 may substantially determine the resolution of the calibration. Accordingly, fine tuning may be performed by making the areas of the second sub-electrodes 12 relatively small in the biosensor 6 according to the present embodiment.

In addition, referring to FIG. 8, in some embodiments, at least some of the plurality of second sub-electrodes 12 may have different areas, and through this, the resolution of the biosensor 6 may be diversified and a desired resolution may be efficiently realized in a process of adjusting the area of a working electrode of the biosensor 6.

Further, in some embodiments, the area of any one of the plurality of second sub-electrodes 12 may be twice as large as the areas of another second sub-electrode 12, and in this case, because the areas of the plurality of second sub-electrodes 12 have a certain relationship, a desired resolution may be efficiently realized in a process of adjusting the area of a working electrode of the biosensor 6.

For example, referring to FIG. 8, when the ratio of the areas of electrode A, electrode B, and electrode C is 10:2:1, that is, when the area of any one of the plurality of second sub-electrodes 12 is twice as large as the area of another second sub-electrode, the magnitude of a current may be adjusted as in the following table.

| Electrode A | Electrode B | Electrode C | Magnitude of current |
| --- | --- | --- | --- |
| Close | Open | Open | I |
| Close | Open | Close | 1.1 × 1 |
| Close | Close | Open | 1.2 × 1 |
| Close | Close | Close | 1.3 × 1 |

That is, in the present embodiment, a resolution of 10% may be realized by using two second sub-electrodes 12 (electrode B and electrode C). In comparison, considering that a minimum of three second sub-electrodes 12 are necessary to adjust the magnitude of a current by using the second sub-electrodes 12 having the same area, it can be identified that when the area of any one of the plurality of second sub-electrodes 12 is twice as large as the area of another second sub-electrode 12, a desired resolution may be efficiently realized in a process of adjusting the area of a working electrode of the biosensor 6 due to the fact that the areas of the plurality of second sub-electrodes 12 have a certain relationship.

Hereinafter, utilization of the biosensor 6 according to the present embodiment will be described with reference to FIG. 10.

That is, in the biosensor 6 according to the present embodiment, an area of the first electrode 10 may be adjusted and calibrated in a hardware way by determining the number of the second sub-electrodes 12, which are not electrically connected to the first sub-electrode 11, of the plurality of second sub-electrodes 12 according to the mixture solution in the reaction chamber 30 in a process of manufacturing the biosensor 6.

Accordingly, an accurate result may be obtained by directly inserting the biosensor 6 according to the inventive concept into a socket 120 of a medical device 100 including a display 110, without performing a separate step for coding by the user or the medical device 100. Because a calibrated result may be obtained according to the area of the first electrode 10, necessary monitoring data may be obtained by detecting an electrochemical signal generated due to a reaction of a target material and a mixture solution.

Figure 11:
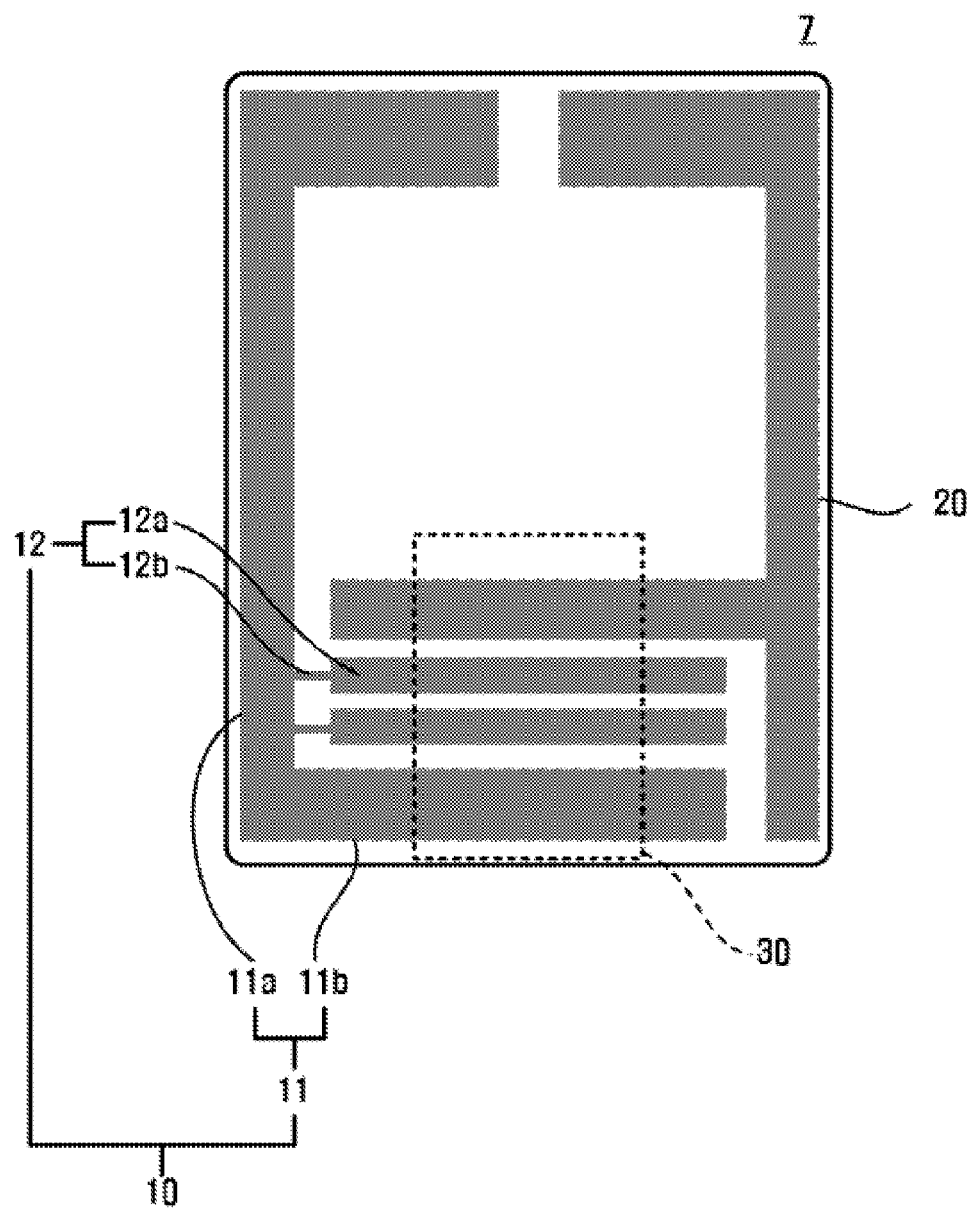
FIG. 11 is a view illustrating a schematic configuration of a non-coding type biosensor according to a seventh embodiment of the inventive concept.

Hereinafter, a non-coding type biosensor 7 according to a seventh embodiment of the inventive concept will be described with reference to FIG. 11. Referring to FIG. 11, a schematic configuration of the non-coding type biosensor 7 according to the seventh embodiment of the inventive concept is illustrated. Meanwhile, a difference from the non-coding type biosensor 6 according to the sixth embodiment of the inventive concept will be mainly described.

Referring to FIG. 11, a plurality of second sub-electrodes 12 may have the same area.

Figure 12:
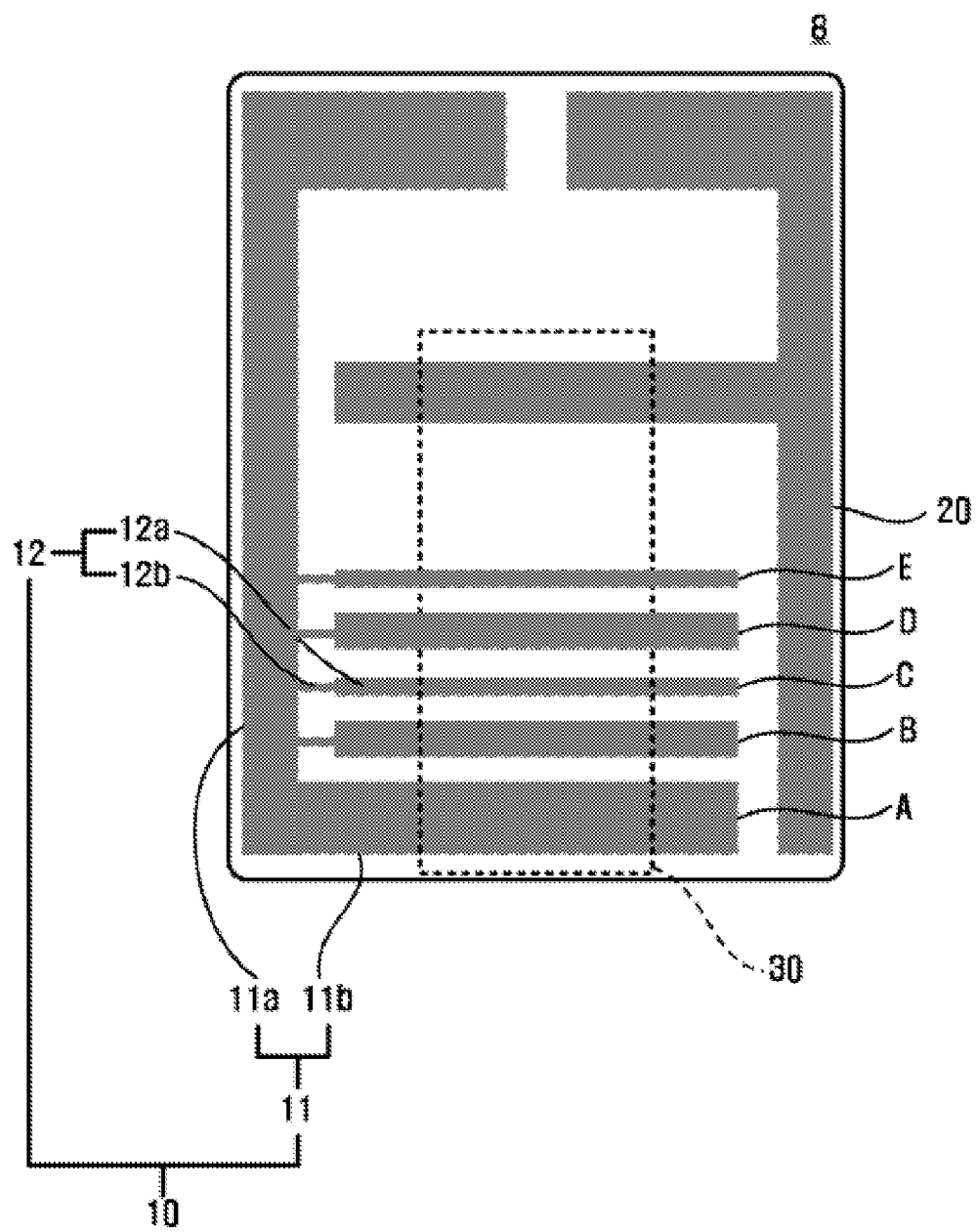
FIG. 12 is a view illustrating a schematic configuration of a non-coding type biosensor according to an eighth embodiment of the inventive concept.

Hereinafter, a non-coding type biosensor 8 according to an eighth embodiment of the inventive concept will be described with reference to FIG. 12. Referring to FIG. 12, a schematic configuration of the non-coding type biosensor 8 according to the eighth embodiment of the inventive concept is illustrated. Meanwhile, a difference from the non-coding type biosensor 6 according to the sixth embodiment of the inventive concept will be mainly described.

Referring to FIG. 12, because the biosensor 8 according to the eighth embodiment of the inventive concept has four second sub-electrodes 12, a range in which the magnitude of a current may be adjusted may be diversified.

Hereinafter, a method for manufacturing the non-coding type biosensor 6 according to the second embodiment of the inventive concept will be described with reference to FIG. 13. Referring to FIG. 13, a flowchart of the method for manufacturing the non-coding type biosensor 6 according to the embodiment of the inventive concept is disclosed. Meanwhile, a repeated description in relation to the non-coding type biosensor 6 will be omitted.

First, a biosensor 6 including first and second electrodes 10 and 20 and a reaction chamber 30 that contacts the first and second electrodes 10 and 20 is provided (S10).

In detail, a biosensor 6 including first and second electrodes 10 and 20 and a reaction chamber 30 that contacts the first and second electrodes 20 may be provided, and a mixture solution that reacts with a target material is located in a reaction chamber 30, wherein the first electrode 10 may be a working electrode and a second electrode 20 may be a reference electrode. Meanwhile, in the present step, a method for producing the first electrode 10, the second electrode 20, the reaction chamber 30, and the mixture solution and its sequence maybe diversified.

In some embodiments, the step of providing the biosensor 6 may be a step of providing a non-coding type biosensor 6 including a first electrode 10 including a first sub-electrode 11 and a plurality of second sub-electrodes 12, the first sub-electrode 11 including a body part 11a and a working part 11b, and a reaction chamber 30 in which a mixture solution that reacts with a target material is located, the reaction chamber 30 contacting the working part 11b and the plurality of second sub-electrodes 12, and ends of the plurality of second sub-electrodes 12 may be connected to the body part 11a as in FIG. 8, but the inventive concept is not limited thereto.

Subsequently, at least one biosensor 6 may be sampled for production batches of a mixture solution contained in the biosensor 6 (S20).

The mixture solution, which is to be contained in the biosensor 6, may be produced, for example, in a plurality of production batches. In this case, a sample of at least one biosensor 6 may be secured for production batches of the mixture solution by sampling at least one biosensor 6 including the mixture solution, which has been produced in each of the production batches.

Subsequently, characteristic information of the sampled biosensor 6 may be drawn (S30).

Here, the step of drawing characteristic information of the sampled biosensor 6 may be a step of analyzing a reaction result occurring in the biosensor 6 by using a control solution for the biosensors 6 sampled for the production batches. In detail, a reaction of the control solution and the mixture solution in the reaction chamber 30 may be induced by injecting the control solution instead of a target material into the sampled biosensor 6, and through this, characteristic information of the sampled biosensor 6 may be drawn by measuring the magnitude of the generated current.

However, in the method for manufacturing a non-coding type biosensor 6 according to the second embodiment of the inventive concept, the step of drawing characteristic information of the sampled biosensor 6 may be a step of drawing characteristics information of the sampled biosensor 6 while all of ends of the plurality of second sub-electrodes 12 are connected to the body part 11a. That is, characteristic information of the sampled biosensor 6 may be drawn while all of the second sub-electrodes 12 in the biosensor 6 function as working electrodes.

In the method for manufacturing the non-coding type biosensor 6 according to the first embodiment of the inventive concept, because the characteristic information of the sampled biosensor 6 is drawn while all of the second sub-electrodes 12 in the biosensor 6 function as working electrodes, the characteristics information of the sampled biosensor 6 is drawn while the areas of the first electrode 10 functioning as a working electrode are maximized.

Accordingly, because the magnitude of a current generated and measured in the present step is maximal, a calibration may be formed by reducing the area of the first electrode 10 of the biosensor 6 such that the measured magnitude of a current may decrease.

Subsequently, considering the production batch in which the mixture solution contained in the biosensor 6 and the drawn characteristic information, the area of the first electrode 10 of the biosensor 6 may be adjusted (S40).

Here, the step of adjusting the area of the first electrode 10 of the biosensor 6, an end of at least one of the plurality of second sub-electrodes 12 is not connected to the body part 11a so that the area of the first electrode 10 may be reduced. For example, the electrode fabricating parts 12b of the second sub-electrodes 12 may be etched through radiation of a laser beam or punching, but the inventive concept is not limited thereto.

In detail, for the biosensor 6 the area of the first electrode 10 of which is to be adjusted, it may be determined how the magnitude of a current will be adjusted, by recognizing a production batch in which the mixture solution contained in the corresponding biosensor 6 has been produced and considering the characteristic information of the sampled biosensor 6 in relation to the mixture solution produced in the corresponding production batch, and accordingly, the area of the first electrode 10 functioning as a working electrode in the biosensor 6 may be determined. Further, in order to satisfy the determined area, the electrode fabricating parts 12b of the second sub-electrodes 12 may be etched.

For example, referring to FIG. 8, when the ratio of the areas of electrode A, electrode B, and electrode C is 7:2:1, the magnitude of a current may be adjusted by determining whether the electrode fabricating parts 12b of the second sub-electrodes 12 will be etched or not as in the following table, and in the present embodiment, the magnitude of the current may be reduced because the magnitude of the current in the drawing characteristic information is a maximum current magnitude.

| Electrode A | Electrode B | Electrode C | Magnitude of current |
| --- | --- | --- | --- |
| Close | Close | Close | I (reference) |
| Close | Close | Open | 0.9 × 1 |
| Close | Open | Close | 0.8 × 1 |
| Close | Open | Open | 0.7 × 1 |

Subsequently, the biosensor 6 the area of the first electrode 10 of which has been adjusted may be packaged (S50).

The step of adjusting the area of the first electrode 10 is one step of the process of manufacturing the biosensor 6, and if the hardware calibration is finished by adjusting the area of the first electrode 10, the manufacturing process of the biosensor 6 may be ended after the biosensor 6 is packaged.

Hereinafter, a method for manufacturing the non-coding type biosensor 6 according to the third embodiment of the inventive concept will be described with reference to FIG. 13. Meanwhile, a difference from method for manufacturing the non-coding type biosensor 6 according to the second embodiment of the inventive concept will be mainly described.

However, in the method for manufacturing a non-coding type biosensor 6 according to the third embodiment of the inventive concept, the step (S30) of drawing characteristic information of the sampled biosensor 6 may be a step of drawing characteristics information of the sampled biosensor 6 while an end of at least one of the plurality of second sub-electrodes 12 is not connected to the body part 11a. For example, characteristic information of the sampled biosensor 6 may be drawn while none of the second sub-electrodes 12 in the biosensor 6 functions as working electrodes.

In the method for manufacturing the non-coding type biosensor 6 according to the third embodiment of the inventive concept, because the characteristic information of the sampled biosensor 6 is drawn while none of the second sub-electrodes 12 in the biosensor 6 functions as working electrodes, the characteristics information of the sampled biosensor 6 is drawn while the areas of the first electrode 10 functioning as a working electrode are minimized.

Accordingly, because the magnitude of a current generated and measured in the present step is minimal, a calibration may be formed by increasing the area of the first electrode 10 of the biosensor 6 such that the measured magnitude of a current may increase in the following step.

Subsequently, considering the production batch in which the mixture solution contained in the biosensor 6 and the drawn characteristic information, the area of the first electrode 10 of the biosensor 6 may be adjusted (S40).

For example, referring to FIG. 8, when the ratio of the areas of electrode A, electrode B, and electrode C is 10:2:1, the magnitude of a current may be adjusted by determining whether the electrode fabricating parts 12*b* of the second sub-electrodes 12 will be etched or not as in the following table, and in the present embodiment, the magnitude of the current may be increased because the magnitude of the current in the drawing characteristic information is a minimum current magnitude.

| Electrode A | Electrode B | Electrode C | Magnitude of current |
| --- | --- | --- | --- |
| Close | Open | Open | I (reference) |
| Close | Open | Close | 1.1 × 1 |
| Close | Close | Open | 1.2 × 1 |
| Close | Close | Close | 1.3 × 1 |

Hereinafter, a method for manufacturing the non-coding type biosensor 6 according to the fourth embodiment of the inventive concept will be described with reference to FIG. 13. Meanwhile, a difference from method for manufacturing the non-coding type biosensor 6 according to the first embodiment of the inventive concept will be mainly described.

However, in the method for manufacturing a non-coding type biosensor 6 according to the fourth embodiment of the inventive concept, the step (S30) of drawing characteristic information of the sampled biosensor 6 may be a step of drawing characteristics information of the sampled biosensor 6 while an end of at least one of the plurality of second sub-electrodes 12 is not connected to the body part 11*a*. For example, characteristic information of the sampled biosensor 6 may be drawn while some of the second sub-electrodes 12 in the biosensor 6 do not function as working electrodes.

In the method for manufacturing the non-coding type biosensor 6 according to the fourth embodiment of the inventive concept, because the characteristic information of the sampled biosensor 6 is drawn while some of the second sub-electrodes 12 in the biosensor 6 do not function as working electrodes, the characteristics information of the sampled biosensor 6 is drawn while the areas of the first electrode 10 functioning as a working electrode are between a maximum value and a minimum value.

Accordingly, because the magnitude of a current generated and measured in the present step is between a maximum value and a minimum value, a calibration may be formed by increasing or decreasing the area of the first electrode 10 of the biosensor 6 such that the measured magnitude of a current may increase or decrease.

Subsequently, considering the production batch in which the mixture solution contained in the biosensor 6 and the drawn characteristic information, the area of the first electrode 10 of the biosensor 6 may be adjusted (S40).

For example, referring to FIG. 12, when the ratio of the areas of electrode A, electrode B, electrode C, electrode D, and electrode E is 7:2:1:2:1, the magnitude of a current may be adjusted by determining whether the electrode fabricating parts 12*b* of the second sub-electrodes 12 will be etched or not as in the following table, and in the present embodiment, the magnitude of the current may be increased or decreased because the magnitude of the current in the drawing characteristic information is between a maximum value and a minimum value.

Further, in the present embodiment, the area of the first electrode 10 may be adjusted such that the working part 11*b* of the first sub-electrode 11 is not electrically connected to the body part 11*a*.

| Electrode A | Electrode B | Electrode C | Electrode D | Electrode E | Magnitude of current |
| --- | --- | --- | --- | --- | --- |
| Close | Close | Close | Open | Open | I (reference) |
| Close | Close | Close | Open | Close | 1.1 × 1 |
| Close | Close | Close | Close | Open | 1.2 × 1 |
| Close | Close | Close | Close | Close | 1.3 × 1 |
| Close | Close | Open | Open | Open | 0.9 × 1 |
| Close | Open | Close | Open | Open | 0.8 × 1 |
| Close | Open | Open | Open | Open | 0.7 × 1 |
| Open | Close | Close | Close | Close | 0.6 × 1 |
| Open | Close | Close | Close | Open | 0.5 × 1 |
| Open | Close | Open | Close | Open | 0.4 × 1 |
| Open | Close | Close | Open | Open | 0.3 × 1 |
| Open | Close | Open | Open | Open | 0.2 × 1 |
| Open | Open | Close | Open | Open | 0.1 × 1 |

Although the embodiments of the inventive concept have been described with reference to the drawings, the inventive concept is not limited thereto. It is understood that the inventive concept may be variously corrected and modified by those skilled in the art without departing from the technical spirit of the inventive concept and the range of equivalents of the claims. Accordingly, the scope of the inventive concept should not be determined by the embodiments and the drawings, but be determined by the claims and the equivalents.

What is claimed is:

1. A non-coding type biosensor comprising:
    a first electrode comprising a first sub-electrode and a plurality of second sub-electrodes that are spaced apart from the first sub-electrode, ends of at least some of the plurality of second sub-electrodes being connected to the first sub-electrode;
    a reaction chamber in which a target material and a mixture solution react with each other, the reaction chamber contacting opposite ends of the plurality of second sub-electrodes; and
    a second electrode of which one end contacts the reaction chamber,
    wherein in the first electrode, at least some of the plurality of second sub-electrodes are not electrically connected to the first sub-electrode.

2. The non-coding type biosensor of claim 1, wherein in the first electrode, the ends of at least some of the plurality of second sub-electrodes are connected to the first sub-electrode through electrode fabricating areas, respectively.

3. The non-coding type biosensor of claim 2, wherein shapes of the electrode fabricating areas are different from shapes of the second sub-electrodes connected to the first sub-electrode.

4. The non-coding type biosensor of claim 1, wherein the number of the second electrodes, which are not electrically connected to the first sub-electrode, of the plurality of second sub-electrodes varies according to a mixture solution in the reaction chamber.

5. The non-coding type biosensor of claim 1, wherein the plurality of second sub-electrodes have the same area.

6. The non-coding type biosensor of claim 1, wherein the at least some of the plurality of second sub-electrodes have different areas.

7. A non-coding type biosensor comprising:
- a first electrode comprising a first sub-electrode and a plurality of second sub-electrodes, the first sub-electrode comprising a body part and a working part; and
- a reaction chamber in which a mixture solution that reacts with a target material is located, the reaction chamber contacting the working part and the plurality of second sub-electrodes respectively,
- wherein ends of at least some of the plurality of second sub-electrodes are respectively connected to the body part.

8. The non-coding type biosensor of claim 7, wherein
- the ends of at least some of the plurality of second sub-electrodes are respectively connected to the body part through electrode fabricating parts, and
- shapes of the electrode fabricating parts are different from shapes of the second sub-electrodes connected to the body part.

9. The non-coding type biosensor of claim 7, wherein an area of the first sub-electrode is larger than areas of the plurality of second sub-electrodes.

10. The non-coding type biosensor of claim 9, wherein the at least some of the plurality of second sub-electrodes have different areas.

11. The non-coding type biosensor of claim 7, further comprising:
- a second electrode that contacts the reaction chamber while being spaced apart from the first electrode,
- wherein the first electrode is a working electrode and the second electrode is a reference electrode.

* * * * *